(12) United States Patent
Tiitta et al.

(10) Patent No.: US 8,124,820 B2
(45) Date of Patent: Feb. 28, 2012

(54) PROCESS FOR THE MANUFACTURE OF POLYOLEFINS

(75) Inventors: Marja Tiitta, Porvoo (FI); Anna-Mari Illikainen, Porvoo (FI); Kari Kulmala, Porvoo (FI); Vesa-Matti Lehtinen, Porvoo (FI); Fredrik Nissfolk, Porvoo (FI)

(73) Assignee: Neste Oil Oyj, Espoo (FI)

( * ) Notice: Subject to any disclaimer, the term of this patent is extended or adjusted under 35 U.S.C. 154(b) by 879 days.

(21) Appl. No.: 11/808,879

(22) Filed: Jun. 13, 2007

(65) Prior Publication Data
US 2007/0293712 A1   Dec. 20, 2007

Related U.S. Application Data

(60) Provisional application No. 60/813,376, filed on Jun. 14, 2006.

(51) Int. Cl.
*C07C 2/12*   (2006.01)

(52) U.S. Cl. ........ 585/510; 585/502; 585/520; 585/530; 585/532; 585/533; 585/254; 585/255

(58) Field of Classification Search ................. 585/254, 585/255, 502, 510, 516, 520, 530, 532, 533; 502/235
See application file for complete search history.

(56) References Cited

U.S. PATENT DOCUMENTS 2,198,937 A   4/1940   Frey et al.
(Continued)

FOREIGN PATENT DOCUMENTS

EP   0673352   9/1995
(Continued)

OTHER PUBLICATIONS

G. W. Gokel, ed., Dean's Handbook of Organic Chemistry (2nd Ed.), McGraw-Hill (2004) on-line version available at: http://knovel.com.*

(Continued)

*Primary Examiner* — In Suk Bullock
*Assistant Examiner* — Bradley Etherton
(74) *Attorney, Agent, or Firm* — Birch, Stewart, Kolasch & Birch, LLP

(57) ABSTRACT

The present invention relates to a process for producing polyolefins wherein a feedstock comprising n-olefin or a mixture of n-olefins is dimerized in the presence of a solid acidic catalyst by passing the feedstock to a catalytic distillation apparatus comprising either a) a combination of a distillation column and a reactor comprising at least one catalyst bed, or b) a distillation column connected to one or more side reactors comprising at least one catalyst layer, recovering the unreacted n-olefin from the distillation column or the combination of the distillation column and the reactor at the upper part thereof as a side-stream to be combined with the feedstock, and the reaction product from the dimerization is hydrogenated.

17 Claims, 4 Drawing Sheets

U.S. PATENT DOCUMENTS

Figure 1:
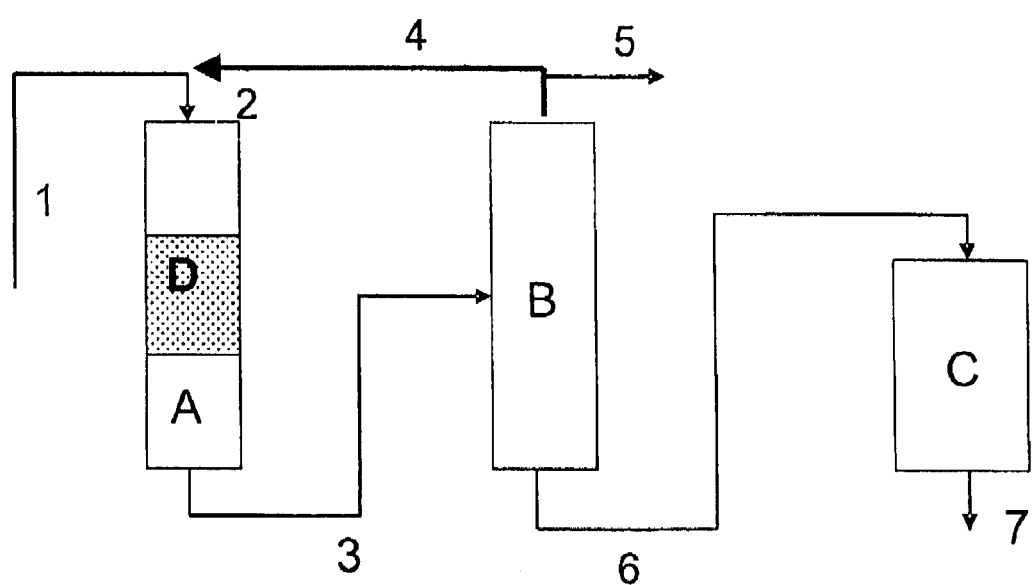

| | | | | |
|---|---|---|---|---|
| 4,300,009 | A | * | 11/1981 | Haag et al. .................... 585/408 |
| 4,417,088 | A | | 11/1983 | Miller |
| 4,935,577 | A | | 6/1990 | Huss, Jr. et al. |
| 5,053,569 | A | | 10/1991 | Marquis et al. |
| 5,120,891 | A | * | 6/1992 | Sanderson et al. ............ 585/533 |
| 5,134,243 | A | * | 7/1992 | Bhore et al. .................. 585/533 |
| 5,453,556 | A | | 9/1995 | Chang et al. |
| 5,518,699 | A | | 5/1996 | Kashnitz et al. |
| 5,714,661 | A | * | 2/1998 | Tuli et al. ...................... 585/533 |
| 5,888,466 | A | * | 3/1999 | Perego et al. ............. 423/330.1 |
| 6,274,783 | B1 | * | 8/2001 | Gildert et al. ................. 585/255 |
| 6,518,473 | B2 | * | 2/2003 | Miller et al. .................. 585/517 |
| 6,703,356 | B1 | * | 3/2004 | Wu .............................. 508/591 |
| 6,703,358 | B1 | | 3/2004 | Wu |
| 6,706,936 | B2 | * | 3/2004 | O'Rear et al. ................ 585/330 |
| 6,841,711 | B2 | * | 1/2005 | Krug et al. .................... 585/326 |
| 2002/0128530 | A1 | | 9/2002 | Miller et al. |
| 2004/0092783 | A1 | | 5/2004 | Ryu |
| 2004/0230085 | A1 | * | 11/2004 | Jakkula et al. ................ 585/240 |
| 2005/0137435 | A1 | | 6/2005 | Tiitta et al. |
| 2007/0123743 | A1 | * | 5/2007 | Ng et al. ....................... 585/260 |

FOREIGN PATENT DOCUMENTS

| | | |
|---|---|---|
| FI | 000096852 | 5/1996 |
| FI | 20041675 | 6/2006 |
| WO | WO-9300165 A1 | 1/1993 |
| WO | WO-94/13599 | 6/1994 |
| WO | WO-0051703 A1 | 9/2000 |
| WO | WO-2007048871 A1 | 5/2007 |

OTHER PUBLICATIONS

C. T. Kresge, et. al. "Molecular Sieves" in Kirk-Othmer Encyclopedia of Chemical Technology, John Wiley, 2004, available on-line Nov. 19, 2004.*

Huang, et al., "Investigation of Synthesizing MCM-41/ZSM-5 Composites" in J. Phys. Chem. B, 2000, 104, 2817-2823.*

D. R. Lide, ed., CRC Handbook of Chemistry and Physics, 91st ed., 2011 Internet version available at http://knovel.com.*

Pater, Jerome P.G. et al., "Oligomerization of Hex-1-ene over Acidic Aluminosilicate Zeolites, MCM-41, and Silica-Alumina Co-gel Catalysts: A Comparative Study," Journal of Catalysis, 1999, vol. 184, pp. 262-267.

European Search Report issued on Oct. 13, 2011 for Corresponding European Patent Application No. 07788742.0.

* cited by examiner

PROCESS FOR THE MANUFACTURE OF POLYOLEFINS

This Nonprovisional application claims priority under 35 U.S.C. §119(e) on U.S. Provisional Application No(s). 60/813,376 filed on Jun. 14, 2006, the entire contents of which are hereby incorporated by reference.

TECHNICAL FIELD

The invention relates to the production of high-grade base oils and to selective dimerization of n-olefins using a solid and acidic catalyst. Particularly, the invention is directed to a process wherein n-olefins are dimerized in a catalytic distillation apparatus, followed by hydrogenation to give polyolefins.

STATE OF THE ART

Saturated olefinic oligomers are a significant group of high-grade synthetic base oils. Poly-alpha-olefins known as PAOs are typically produced by oligomerization of alpha-olefins in the presence of homogeneous Friedel-Crafts catalysts, such as boron trifluoride ($BF_3$) and a promoter at slightly elevated $BF_3$ pressures, and temperatures below 100° C. Water or an alcohol normally serves as the promoter. In the PAO process, 1-decene is typically used as the feedstock, mainly giving trimers and tetramers of the feedstock olefin as the product.

Base oils may also be produced by dimerization of n-olefins heavier than decene. Base oils of the PIO (poly(internal olefin)) group are produced by dimerization of internal n-olefins, typically $C_{15}$-$C_{16}$ n-olefins, using $BF_3$ catalysts. Among the products of the PIO process, dimers are particularly suitable feedstocks for base oil production.

A catalyst separation step is always necessary in PAO and PIO processes using homogeneous catalysts.

As is known, n-olefins refer to linear olefins or linear olefins with no more than one branch, that is, to slightly branched olefins.

Oligomerization refers to a reaction where molecules of at least one type react with each other resulting in the increase of the molecular weight, said increase being the added molecular weight of at least three molecules. Oligomerization may be illustrated with the following equation:

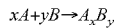

$$xA + yB \rightarrow A_xB_y$$

where A may be identical with or different from B, x is 0 or an integer, y is 0 or an integer, x+y>2, $\Sigma x = n$, $\Sigma y = m$, A and B are olefinic molecules, and n and m are integers. The term oligomer refers to a repetitive combination of monomeric units of at least the one type, the number of said units ranging from 3 to 100.

The term dimerization refers to a reaction where molecules of at least one type react with each other resulting in the increase of the molecular weight, said increase being the added molecular weight of at least two molecules. Dimerization may be illustrated with the following equation:

$$A + B \rightarrow AB$$

where A may be identical with or different from B, A and B being olefinic molecules. The term diner refers to a combination of two monomeric units of at least one type.

The term polyolefin refers to a combination comprising at least two olefinic monomeric units of at least one type.

Several alternative heterogeneous catalysts for the dimerization of heavy olefins are known e.g. from U.S. Pat. No. 4,417,088, U.S. Pat. No. 5,053,569, U.S. Pat. No. 5,453,556 and U.S. Pat. No. 6,703,356. In addition to the desired dimerization reaction, the use of said heterogeneous acid catalysts disclosed in said documents resulted in cracking and isomerization reactions of the feedstock olefins, as well as formation of heavier oligomers, mainly trimers and tetramers. Particularly detrimental isomerization reactions of the feedstock olefins include reactions yielding products that may not be dimerized, such as naphthenes. Attainable yields of the base oil are lowered by the cracking products formed as well as naphthenes resulting from the isomerization of monomeric olefins. Because relatively valuable olefin are used as the process feedstock, any undesirable side reactions thereof also have a considerable impact on the feasibility of the process.

The document U.S. Pat. No. 5,053,569 discloses the dimerization of α-olefins using an acidic calcium/montmorillonite catalyst. The document U.S. Pat. No. 6,703,356 discloses an oligomerization process of alpha-olefins using alpha-olefins with a carbon number ranging between 10 and 30, or a mixture thereof as the feedstock. The catalyst is specified as a crystal catalyst having a constraint index of less than 3. The constraint index is a measure of the product selectivity of the catalyst. In the examples, 1-hexadecene, 1-tetradecene and 1-octadecne are used as feedstocks, whereas MCM-22, MCM-56, USY, Beta, ZSM-12 and $WO_x$/on $ZrO_2$ are used as catalysts.

In the examples of the above documents U.S. Pat. No. 5,053,569 and U.S. Pat. No. 6,703,356, highest conversions attained in the dimerization of heavy olefins using heterogeneous acid catalysts are 92% and 87%. A conversion of clearly below 100% may be attributed to the formation of naphthenes from feedstock olefins. The product obtained in the examples of the document U.S. Pat. No. 5,053,569 contained trimers and heavier oligomers in a total amount of 47%, which is not desirable for the properties of the base oil product. Selectivity for dimers is higher (70%) in the example described in the document U.S. Pat. No. 6,703,356, having a high conversion (87%), yet high amounts of cracked products (4%) were obtained.

The term catalytic distillation refers generally to the combination of a chemical reaction with the product separation. The reaction and product separation are carried out together in an inseparable manner. A catalytic distillation apparatus normally comprises a distillation column incorporating one or more catalytic zones. In said catalytic zones, streams from a specified level or plate of the distillation column are treated to give desired reaction products. Thereafter, the product stream is fractionated using a distillation means. Said catalytic zone may be placed within or outside the distillation means. In industrial applications, catalytic distillation is used in the production of ethers, said process being also known e.g. for dehydration of alcohols, and oxydation of paraffins.

Use of the catalytic distillation is also known in the oligomerization process. U.S. Pat. No. 4,935,577 discloses an oligomerization process wherein alpha-olefins having from 3 to 12 carbon atoms are passed to a distillation column containing Lewis acid catalyst for the reaction. The temperature of the catalytic distillation apparatus is no more than about 150° C., the typical operation temperature range being below 50° C. A combination catalyst is used in the distillation apparatus, and accordingly, a unit for the separation of the Lewis acid prior to recycling to the distillation apparatus is an essential part of the apparatus U.S. Pat. No. 2,198,937 discloses an apparatus comprising a distillation column and a side reactor for the polymerization of hydrocarbons. The apparatus may be operated under conditions similar to those in catalytic distillation.

The document FI 96852 discloses a process and an apparatus for oligomerizing olefins. In this process, $C_3$-$C_{20}$ olefins or mixtures thereof are passed to a catalytic distillation system where the feedstock olefins are contacted with a catalyst at a temperature of above 150° C., thus yielding a product containing oligomers. The catalyst used in this process mainly consists of zeolite, the products formed being middle distillates and lubricants. The catalytic distillation system used in the process may also be a distillation column for the product separation, connected to at least one side reactor containing the catalyst.

Based on above teachings it may be seen that there is an obvious need for a novel improved process for the production of polyolefins from n-olefins, said novel process eliminating or at least substantially reducing problems and deficits associated with the solutions of the state of the art.

OBJECTS OF THE INVENTION

An object of the invention is to provide a process for the production of polyolefins from n-olefins.

Another object of the invention is to provide a process for the production of polyolefins from n-olefins using a solid acidic catalyst.

Still another object of the invention is to provide a process for the production of polyolefins from $C_8$-$C_{30}$ n-olefins using a solid acidic mesoporous catalyst.

Further, an object of the invention is to provide a process for the dimerization of $C_8$-$C_{30}$ n-olefins using a solid acidic mesoporous catalyst to give polyolefins.

An object of the invention is also a process for producing a base oil component.

Yet another object of the invention is the use of a catalytic distillation apparatus for the dimerization of n-olefins, particularly $C_8$-$C_{30}$ n-olefins.

An object of the invention is also to provide di-n-olefins consisting of two identical or different n-olefins having carbon chain lengths of C8-C30.

SUMMARY OF THE INVENTION

The present invention relates to a process for producing high-grade products useful as base oils and base oil components from n-olefins using a solid and acidic catalyst, by dimerizing an n-olefin or a mixture of n-olefins in a catalytic distillation apparatus, wherein the catalyst is placed into a distillation column or into a side reactor outside the distillation column, followed by hydrogenation of the product. In the process of the invention, the feedstock comprising an n-olefin or a mixture of n-olefins, is dimerized in the presence of a solid acidic catalyst by passing the feedstock to a catalytic distillation apparatus either comprising a) a combination of a distillation column and a reactor having at least one catalyst layer, or b) a distillation column connected to one or more side reactors having at least one catalyst layer, recovering the unreacted n-olefin at the upper part of the distillation column or the combination of the distillation column and the reactor as a side-stream to be combined with the feedstock, whereas the reaction product from the dimerization is hydrogenated. Impurities still present in the dimerization product or final product may optionally be removed using an additional distillation step.

Figure 2:
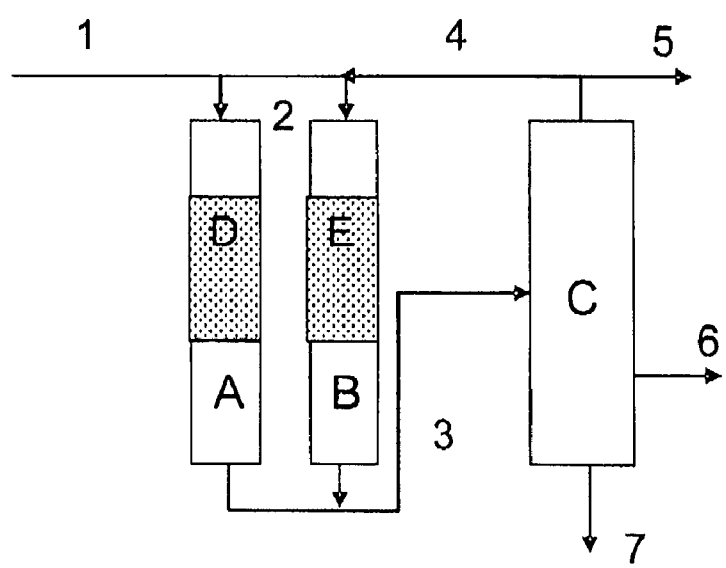
Figure 3:
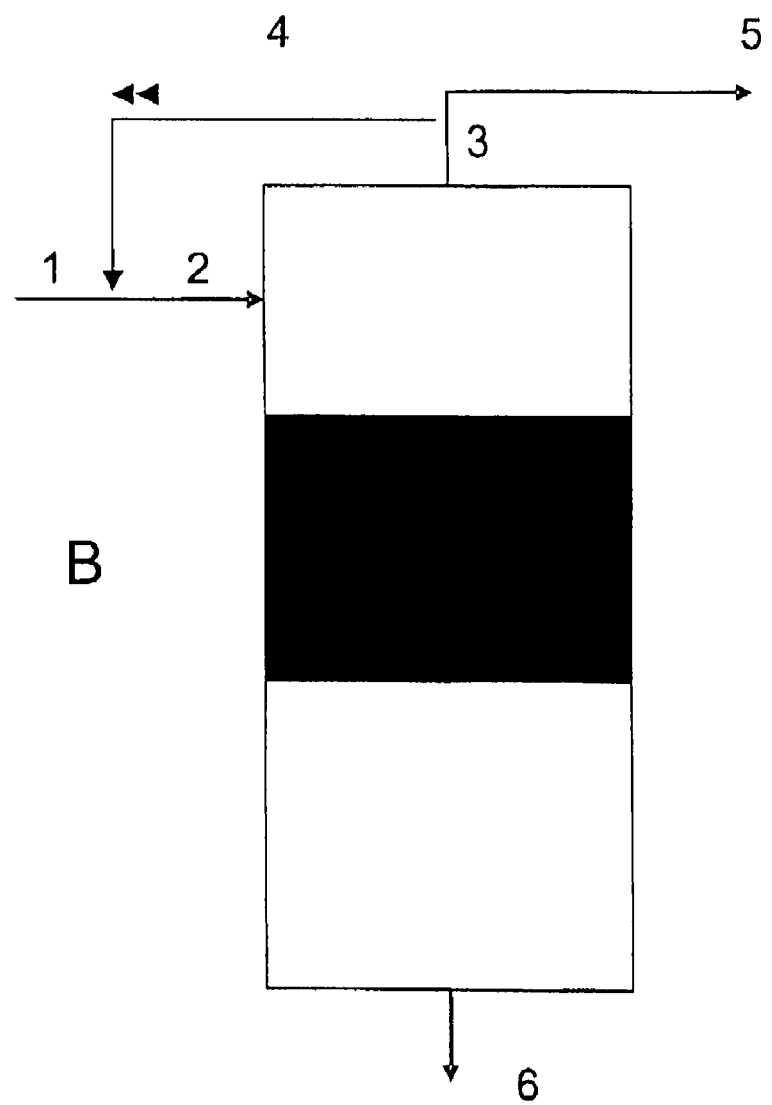

The invention and some alternative embodiments thereof are illustrated by appended FIGS. 1, 2 and 3, however, without wishing to limit the invention to these presented embodiments.

FIGURES

FIG. 1 schematically shows an embodiment of the invention for producing a base oil component.

FIG. 2 schematically shows an embodiment of the invention wherein the dimerization of n-olefins is carried out in a catalytic distillation apparatus with the catalyst in separate side reactors.

FIG. 3 schematically shows an embodiment of the invention wherein the dimerization of n-olefins is performed in a combination of a distillation column and a reactor.

Figure 4:
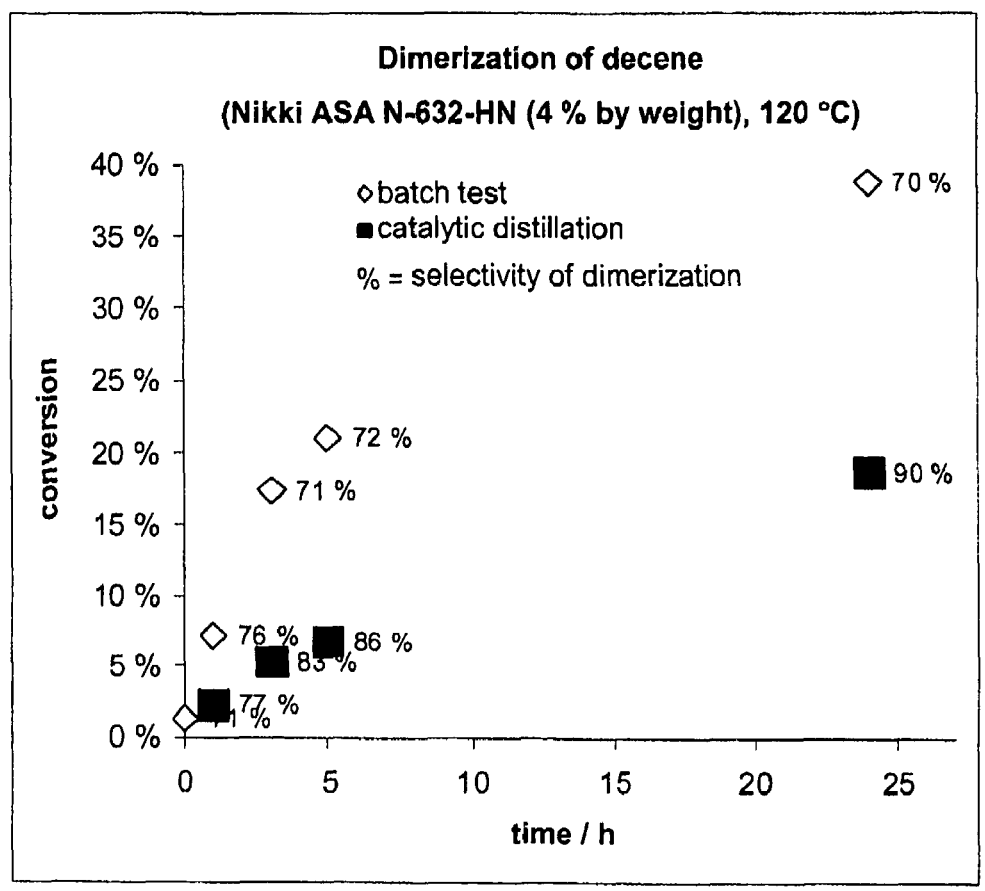

FIG. 4 describes dimerization of decene based on conversion over time as carried out in a batch reactor at a temperature of 120° C. or in a catalytic distillation reactor at the same temperature.

FIG. 1 is a schematic presentation of the basic solution of the inventive process. The feedstock of the process, or stream 1, containing $C_8$-$C_{30}$ n-olefins or a mixture thereof is obtained from a feed tank (not shown in the figure). Stream 4 recovered at the upper part of a distillation column B is combined with stream 1. Streams 1 and 4 together form the stream 2, which is passed to side reactor A containing the dimerization catalyst layer/bed D. Stream 3 is obtained as the product of the side reactor A, said stream 3 containing $C_8$-$C_{30}$ n-olefin monomers and as reaction products mainly dimeric products. Stream 3 is passed to a distillation column B where $C_8$-$C_{30}$ n-olefin monomers rise to the upper part of said distillation column B, followed by recycling the n-olefin monomer fraction thus obtained as stream 4 to the side reactor A in the reaction stage. Stream 5 is removed at the top of the distillation column B, said stream 5 containing components of non-dimerizable monomer fraction in the upper part of the distillation column. With stream 5 the accumulation of the components of non-dimerizable monomer fraction such as branched compounds is prevented in the catalytic distillation apparatus. The product in the form of a product stream 6 mainly consisting of dimers is obtained from the bottom of the distillation column B, said stream 6 being passed to a hydrogenation reactor C. In the hydrogenation reactor C, olefins are hydrogenated to give the product, suitable as a base oil component, followed by the removal of said product from the hydrogenation reactor C as the product stream 7.

In FIG. 2, a preferable solution of the process of the invention is shown. In this solution, a catalytic distillation apparatus having dimerization catalyst layers D and E placed in separate side reactors A and B is used. The feedstock of the process, or stream 1, containing $C_8$-$C_{30}$ n-olefins or a mixture thereof is obtained from a feed tank (not shown in the figure). Stream 4 recovered at the upper part of a distillation column C is combined with stream 1. Streams 1 and 4 together form the stream 2 being either passed to a side reactor A or side reactor B. Stream 2 is passed to the side reactor containing fresh catalyst or regenerated catalyst. Simultaneously, the other side reactor contains the exhausted catalyst, or the catalyst is being regenerated. There are two side reactors in the system, and accordingly, it is not necessary to shut down the process due to lowered catalytic activity. Stream 3 is obtained as the product of the side reactor A or B, said stream 3 containing $C_8$-$C_{30}$ n-olefin monomers and as reaction products mainly dimeric products. Stream 3 is passed to a distillation column C where $C_8$-$C_{30}$ n-olefin monomers rise to the upper part of said distillation column C, followed by recycling the n-olefin monomer fraction thus obtained as stream 4 to the side reactor A or B in the reaction stage. Stream 5 is removed at the upper part of the distillation column C, said stream containing components of non-dimerizable monomer fraction at the upper part of the distillation column C. Accumulation of the components of non-dimerizable monomer fraction such as branched compounds in the catalytic distillation apparatus is prevented by stream 5. From the lower part of the distillation column C, a product stream 6 mainly consisting of dimers, subsequently passed to a hydrogenation reactor for hydrogenation (not shown in the figure), and a bottom product 7 are obtained.

FIG. 3 shows another preferable solution of the inventive process, using a catalytic distillation apparatus having the dimerizing catalyst layer B placed inside the distillation column A. The feed stream 1 comprising $C_8$-$C_{30}$ n-olefins or a mixture thereof is combined with the n-olefin monomer fraction 4 from the top of the distillation column A to give a stream 2 for passing to the distillation column A, to the upper part of the catalyst layer B. In the distillation column A, the feed passes to the catalyst layer B, in which the dimerization reaction mainly proceeds. In the catalyst layer B, n-olefin monomer is in the form of a vapour/liquid mixture and the liquid n-olefin monomer washes the dimers and oligomers formed from the catalyst. n-olefin monomer fraction 3 is obtained from the top of the distillation column A, said fraction being split to give a monomer fraction 4 to be recycled to the reactor, and a monomer stream 5. Accumulation of non-dimerizable components of the monomer fraction in the catalytic distillation apparatus is prevented by removal of said monomer stream 5. The product in the form of a dimer stream 6 is obtained from the bottom of the distillation column A, said stream 6 being passed to a hydrogenation reactor (not shown in the figure) for hydrogenation.

The catalytic distillation apparatus comprises either a) a combination of a distillation column and a reactor having at least one catalyst layer, or b) a distillation column connected to one or more side reactors having at least one catalyst layer.

DETAILED DESCRIPTION OF THE INVENTION

It was surprisingly found that the use of a catalytic distillation apparatus with a solid acidic catalyst allows for the selective dimerization of n-olefins to give base oil useful as a lubricant, or base oil component, with an excellent yield that may even be above 95%. In the process of the invention, the dimerization of n-olefins or n-olefin mixtures to yield dimers is performed in a catalytic distillation apparatus comprising either a) a combination of a distillation column and a reactor comprising at least one catalyst layer, or b) a distillation column connected to one or more side reactors comprising at least one catalyst layer, said catalyst being in the side reactor outside the distillation column. In this way, the temperature of the dimerization reaction may be maintained low, typically below 150° C., thus preventing the formation of naphthenes and cracking of products. Dimerization is followed by hydrogenation to produce the base oil component. Optionally after the dimerization and/or hydrogenation, the product may, if necessary, be passed to a distillation apparatus where any monomer residues are removed from the dimerized product, or the dimers are separated from heavier trimers and tetramers.

The quality of the base oil and/or base oil component obtained as the product useful as a lubricant, after hydrogenation is excellent due to, among other things, low number of undesirable reactions.

In the process of the invention, n-olefin or a mixture of n-olefins is passed to a catalytic distillation apparatus where the single conversion of n-olefins may be suitably controlled. The term single conversion refers to the conversion of an n-olefin to give another compound during the reaction stage. Single conversion of n-olefin monomers is defined as follows:

Single conversion of n-olefin monomers (%)=100× (proportion of n-olefins in the feedstock prior to the reaction stage−proportion of n-olefins in the product after the reaction stage)/proportion of n-olefins in the feedstock prior to the reaction stage.

In the process of the invention, it is preferable to use recycling of the monomeric olefins particularly in embodiments where the catalyst is placed in a side reactor. In this case, total conversion and dimerization selectivity are improved by efficient recycling of the monomeric olefins. A requirement for the efficient recycling of the monomeric olefins is the adjustment of the reaction conditions to values preventing undesired side reactions such as cracking and isomerization of the monomer resulting in naphthenes. Moreover, relatively low single conversion between 5 and 50% is another requirement for high dimerization selectivity meaning selectivity ranging approximately between 80 and 100%. In the process of the invention, high total conversion, ranging between 95 and 100%, is attained with efficient recycling, in spite of the relatively low single conversion. Efficient recycling means that the extent of recycling is such that between 50 and 95% of the original monomer stream contacts the catalyst layer more than once. Extent of recycling refers to the level of the stream passed from the separation step to the catalyst layer. Dimensioning of the components of the apparatus, and thus the investment costs depend on the level of said stream, and therefore, reasonable extent of recycling is preferable for said investment costs. Also energy consumption of the process is influenced by the extent of recycling.

Single conversion is adjusted to a suitable value on the basis of the carbon number. Suitable single conversion means that the extent of side reactions such as formation of heavier oligomers and cracking is adjusted to be low, that is less than 10% of the total conversion of the monomeric olefins is due to side reactions. Reduced formation of heavy oligomers has a positive impact on the properties of the base oil product, and retards the deactivation rate of the catalyst.

The process of the invention is now described in more detail. In the process, the feedstock is passed to a catalyst layer in a catalytic distillation apparatus, either above the catalyst layer in a distillation column where the feedstock migrates to the catalyst layer, or to a catalyst layer in a side reactor, followed by passing the reaction mixture to a distillation column or to a lower part of the distillation column where the monomer fraction migrates to a higher part of the distillation column, and any impurities present in the monomer lighter than the monomers in the distillation range leave the distillation column at the top thereof or may be removed in a subsequent separation unit downstream of the distillation column, and any impurities present in the monomer heavier than the monomers in the distillation range are removed from the column at the bottom or may be removed from the bottom product in a separate separation unit.

The dimerization reaction and some simultaneous oligomerization proceed in the catalyst bed. A monomeric fraction such as n-hexadecene with a boiling point between 280 and 290° C./1 atm, rises in the column as the lighter component upwards from the feeding plate and is removed from the distillation column, typically at the top thereof as a side stream to be recycled and combined with the feedstock. The dimer produced as the raw product, e.g. $C_{32}$ olefin, migrates downward in the distillation column, followed by separation of the dimer stream at a lower part thereof. Oligomerization product such as $C_{48+}$ olefin is obtained as the bottom product stream. In case unreacted olefins and side reactions such as formation of naphthenes corresponding to monomers with respect to their carbon number may not be totally avoided, accumulation thereof in the process streams may, however, be prevented by removing part of the side stream to be recycled at the upper part of the distillation column.

A solvent or solvent mixture may be added to the feedstock, thus retarding deactivation of the dimerization catalyst. The solvent is selected among hydrocarbons such as n-paraffins, isoparaffins and aromatic solvents. The solvent may be removed from the distillation column as a respective side stream via cooling to a separation unit where the solvent is separated from the reaction product. The solvent may also be recycled in the catalytic distillation apparatus without a separate separation unit.

The feedstock may be optionally dried for removal of any water and other impurities present therein. Drying may be carried out with known drying means such as with commercially available molecular sieves e.g. zeolite 3A molecular sieve used for drying hydrocarbons, or using other suitable known methods.

Process feedstock comprises at least one n-olefin selected from the group consisting of $C_8$-$C_{30}$ n-olefins. Examples of suitable n-olefins include 1-decene, mixture of decenes, 1-dodecene, mixture of dodecenes, 1-hexadecene, mixture of hexadecenes, 1-octadecene, mixture of octadecenes, and $C_{20}$-$C_{22}$ 1-olefins, preferably 1-hexadecene, or a mixture of hexadecenes. n-Olefins may be synthetic olefins or olefins of biological origin, produced from biological starting materials such as vegetable oil and animal fats.

In case a catalytic distillation apparatus where the catalyst is placed in a side reactor outside the distillation column is used in the dimerization step of the process of the invention, the feedstock such as 1-hexadecene is directly introduced into the catalyst layer in the side reactor where a diner is produced. The product stream of said side reactor is passed to a distillation column where the monomer fraction such as n-hexadecene having a boiling point between 280 and 290° C./1 atm will rise upward as the lighter component in the distillation column from the feeding plate and is removed, typically at the top of the column as a side stream and recycled to the side reactor. The dimer formed as the reaction product such as $C_{32}$ olefin migrates downward in the distillation column, the dimer stream being separated at a lower part thereof. An oligomerization product such as $C_{48+}$ olefin is obtained as the bottom product stream.

The dimer product obtained above and the bottom product produced as the byproduct are hydrogenated in a hydrogenation step operated continuously or batch wise in the presence of hydrogen. Known hydrogenation catalysts containing metals from the groups VIII and/or VIA of the Periodic System of the Elements may be used. Preferable hydrogenation catalysts include supported Pd, Pt, Ni, Cu, CuCr, NiMo or CoMo catalysts, the support being preferably alumina and/or silica. The hydrogenation step is carried out at a pressure of 5 to 100 bar, preferably at 10 to 70 bar, and at a temperature of 100 to 400° C., preferably at 150 to 250° C.

In the dimerization step of the process of the invention, the temperature in the distillation column or in the catalyst layer of the side reactor ranges between 25 and 200° C., preferably between 50 and 150° C. Pressure range varies according to the carbon number of the feedstock and reaction temperature, and further, the location of the catalyst either in the catalytic distillation apparatus or in a side reactor has an impact on the pressure range. The pressure range thus varies from reduced pressures to elevated pressures. The pressure may vary between 0.001 mbar and 50 bar, preferably 0.5 bar and 30 bar, particularly preferably between 1 mbar and 20 bar. WHSV is properly adjusted on the basis of the single conversion and deactivation rate of the catalyst. WHSV typically ranges between 0.1 and 50 h$^{-1}$ with respect to the feedstock, preferably between 0.5 and 20 h$^{-1}$.

Selection of the pressure of the dimerization reaction as a function of the temperature is illustrated in the table 1 below. Table 1 shows the vapour pressure of 1-decene as a function of the temperature. In case the desired reaction temperature in the catalyst layer of the catalytic distillation apparatus is 50° C., the pressure is selected to be 11 mbar, or in case the desired temperature in the catalyst layer of the catalytic distillation apparatus is 150° C., the pressure is selected to be 580 mbar.

TABLE 1

Vapour pressure of 1-decene at different temperatures

| Temperature/° C. | Pressure/mbar |
|---|---|
| 50 | 11 |
| 100 | 112 |
| 150 | 580 |

If a catalytic distillation apparatus where the catalyst is placed in a side reactor is used, the pressure of the reactor is selected to give the product mixture in liquid phase.

High-grade base oil or a base oil component may be produced by the process of the invention from n-olefins using a solid and acidic catalyst not requiring parts of the catalyst to be subsequently separated and recycled to the distillation apparatus. Moreover, solid acidic catalysts always result in isomerization of double bonds. Particularly suitable solid acidic catalysts include catalysts having a mesopore surface area of above 100 m$^2$/g as measured by nitrogen adsorption and calculated with the following BJH equation:

$$V_{pn} = r_{pn}^2 \times \Delta V_n / (r_{kn} + \Delta t_n)^2 - r_{pn}^2 \times \Delta t_n \times \text{summa}(r_{pj} - t_j \times A_{pj}/r_{pj})$$

where j=1 to n−1; $A_p = 2 \times V_p / r_p$, V is volume, r is diameter of the pore, t is time, A is surface area and n is number of nitrogen layers adsorbed.

Suitable solid acidic catalyst materials include materials having a mesopore surface area based on the BJH equation of more than 100 m$^2$/g, preferably more than 300 m$^2$/g. Such materials comprise amorphous aluminium silicates, preferably acidic amorphous aluminium silicates, and particularly preferably acidic amorphous aluminium silicates with Brönsted acidic sites; zeolites, preferably dealuminated Y zeolites; and mesoporous materials with a regular porous structure, containing silicon and aluminium, among which mesoporous molecular sieves with inserted zeolite are preferable. The zeolite is preferably ZSM-5, beta-zeolite or MCM-22, whereas the mesoporous molecular sieve is MCM-41 with a regular molecular structure. The acidic solid catalyst material is particularly preferably a mesoporous molecular sieve with imbedded MCM-22 zeolitic structures.

The expression mesoporous molecular sieve imbedded with zeolite refers to a catalyst having mesoporous molecular sieve structure and zeolitic structure in the same material and where said mesoporous molecular sieve structure and zeolitic structure are bonded together through a chemical bond. The mesoporous molecular sieve with imbedded zeolite, and the production thereof is disclosed in the patent application FI 20041675.

The aluminium content of the catalyst material varies between 0.2 and 30% by weight as determined by aluminium content assays, while the level of the acid sites varies between 50 and 500 µmol/g as determined by the analysis according to the $NH_3$-TPD method. Suitable catalyst materials have Brönsted acidity, the level thereof being more than 10 µmol/g as measured by the proton NMR method. The mesoporous surface area of the catalyst material as calculated with the BJH equation is more than 100 m²/g, preferably more than 300 m²/g.

The catalyst also comprises a support material to provide a readily mouldable catalyst with mechanical resistance. Said support material is typically an inorganic oxide such as alumina or silica.

In the process of the invention, the olefins and isomers of the olefins in the feedstock are preferably recycled, and the dimerized and oligomerized fractions thus produced are obtained as products from the bottom or as a side stream. In this manner, the total conversion in the process is high, preferably more than 95%, and more than 99% at best.

An apparatus comprising 1) an optional drying means for the feedstock, 2) a catalytic distillation apparatus comprising either a) a combination of a distillation column and a reactor having at least one catalyst layer, or b) a distillation column connected to one or more side reactors having at least one catalyst layer, 3) hydrogenation reactor and optionally a distillation column upstream and/or down-stream of the hydrogenation reactor, is suitable for the process of the invention, and particularly for dimerization of $C_8$-$C_{30}$ n-olefins.

Regeneration of the deactivated dimerization catalyst may be performed in the same reactor as the dimerization reaction. The regeneration is carried out at an elevated temperature using a gaseous mixture that may contain oxygen. During the regeneration, the temperature is equal or higher than that of the dimerization reaction. Thermal resistance of the catalyst and the feasibility of the process are influenced by the maximum regeneration temperature, lower regeneration temperatures being preferable with respect to energy consumption. However, the regeneration temperature should be sufficiently high for the removal of coal formed and any impurities adsorbed in the catalyst.

The process of the invention is endowed with several advantages. The process is continuous, and thus continuous production of the base oil component is possible without interruptions typical for batch reactors.

In the process of the invention, the reactor feedstock may be adjusted as desired since the composition may be controlled very precisely at the side exit of the distillation column. It is thus possible to provide the reactor with a stream containing only a monomer fraction without any lighter or heavier fractions due to possible unselective reactions, said lighter or heavier fractions yielding products with undesirable carbon numbers during the reaction stage.

Desired compositions are obtained as the reactor products since the outlet sites for the products may be selected. This is particularly useful in cases where a mixture of n-olefins having different carbon numbers serves as the feedstock.

It was surprisingly found that selective dimerization of olefins is provided at a reaction temperature below 150° C. Selective dimerization means here a dimerization selectivity of more than 80%. Dimer yields are remarkably high since any unreacted monomer present in the reaction product may be recycled to the feedstock for the reactor by adjusting the recycle ratio.

Reactive components may be immediately separated in the distillation column, and thus side reactions detrimental to the process may be quickly stopped. Other separation units e.g. two distillation columns are not necessary in the process for concentration of the feedstock and the reaction product since the concentration of the product and fractionation of the feedstock may be carried out in the same column, which accordingly results in a simpler apparatus and lower investment costs. In addition, the regeneration of the dimerization catalyst may be performed in the same reactor as the reaction.

The invention is now illustrated with the following examples without wishing to limit the scope thereof.

EXAMPLES

Example 1

Comparative Example

Dimerization of Olefins in a Batch Reactor

Dimerization process was performed in a batch reactor using 1-hexadecene (Neodene 16®). The process temperature was 200° C., the reactor pressure being 20 bar. The amount of the feedstock was 50 g, and that of the catalyst 2 g. The total reaction time was 24 hours. Commercially available Y zeolite (TOSOH Co.), beta-zeolites (TOSOH Co.) and a mesoporous material MCM-41 (produced according to a method disclosed in Catalysis Letters 36 (1996) 103) were used as catalysts. Total $C_{16}$ conversion (=conversion of $C_{16}$ hydrocarbons to give products having a carbon numer of ≠16) and selectivities for different reaction products are shown in the table 2 below.

TABLE 2

Dimerization of 1-hexadecene in a batch reactor

| | Catalyst | | | |
|---|---|---|---|---|
| | Beta | Beta | Y | H-MCM-41 |
| Total $C_{16}$ conversion/(%) | 48.3 | 76.9 | 76.0 | 72.7 |
| Selectivity/(%) | | | | |
| light products (<C16) | 18.1 | 14.3 | 0.8 | 3.2 |
| $C_{16}$-$C_{32}$ | 24.1 | 19.8 | 0.4 | 0.0 |
| dimers | 47.8 | 52.2 | 83.4 | 62.6 |
| trimers | 8.8 | 10.7 | 15.0 | 30.4 |
| heavier (>C48) | 1.2 | 2.9 | 1.2 | 3.8 |

Dimerization of 1-decene was also performed in a batch reactor. The process temperature was 120° C., the reactor pressure being 20 bar. Commercially available aluminium silicate catalyst (Nikki Chemical Co. Ltd) was used as the catalyst, in an amount of 4% by weight of the feed. The results are shown in the FIG. 4. The results indicate that the dimerization selectivity was clearly lower in the batch reactor in comparison to the selectivity of the process of the invention.

Example 2

Dimerization in a System Corresponding to a Catalytic Distillation Apparatus, Comprising Dimerization in a Flow Reactor and Distillation a) Dimerization in a Flow Reactor 1-Hexadecene (Neodene 16®) was introduced at a rate of 10 g/h into a flow reactor (1 bar (a)). The flow reactor was packed with 5 g of aluminium silicate catalyst (Nikki Chemical Co. Ltd) with an aluminium content of 13% by weight, the number of acid sites of 120 µmol/g, and mesoporous surface area >300 m²/g, diluted with silicon carbide (V(catalyst):V(SiC)=1:3), followed by the dimerization reaction at a temperature of 120° C. in the reactor. The dimerization product was collected into a product container. Results of the dimerization, that is, total $C_{16}$ conversion and selectivities for different reaction products are shown in the table 3 below.

TABLE 3

Dimerization of 1-hexadecene in a flow reactor (120° C.)

| | Time (TOS)/h | | |
|---|---|---|---|
| | 6 | 24 | 48 |
| Total $C_{16}$ conversion/(%) | 52.6 | 46.6 | 41.7 |
| Selectivity/(%) | | | |
| light products (<C16) | 0.0 | 0.0 | 0.0 |
| $C_{16}$-$C_{32}$ | 0.0 | 0.0 | 0.0 |
| dimers | 82.1 | 84.4 | 86.5 |
| trimers | 14.5 | 13.0 | 11.7 |
| heavier (>C48) | 3.5 | 2.6 | 1.7 |

TOS = time of stream

The conversion of the $C_{16}$ hydrocarbons declined the longer the catalyst remained in the hydrocarbon stream. Accumulation of heavy hydrocarbon oligomers in the catalyst (coke formation) was a reason to the reduced conversion.

b) Distillation of the Products

The experiment of a) was repeated, and the products obtained from the experiments (1766 g) were pooled. The unreacted monomer fraction (1103 g), middle fraction containing $C_{20}$-$C_{30}$ hydrocarbons (9 g), dimer fraction (452 g) and heavy bottom product (199 g) were separated from said pooled products by distillation.

c) Recycling of the Monomers/Dimerization

The monomer fraction obtained above was used as the feedstock in dimerization. The distilled monomer fraction mainly consisted of internal $C_{16}$ olefins. The composition of the distilled monomer fraction is shown in the table 4 below in the form of surface area percentages as measured by GC-MS-analysis.

TABLE 4

Composition of the distilled monomer fraction

| Component | % |
|---|---|
| branched $C_{14}$ olefins | 0.1 |
| 1-tetradecene | 0.1 |
| other internal $C_{14}$ olefins *) | 0.5 |
| trans-2-tetradecene | 0.1 |
| branched $C_{16}$ olefins | 8.7 |
| 1-hexadecene | 13.6 |
| other internal $C_{16}$ olefins *) | 60.7 |
| trans-2-hexadecene | 9.8 |
| cis-2-hexadecene | 3.5 |
| branched $C_{18}$ olefins | 0.9 |
| 1-octadecene | 0.3 |
| other internal $C_{18}$ olefins *) | 1.4 |
| trans-2-octadecene | 0.2 |
| cis-2-octadecene | 0.1 |
| 1-eicocene + other internal $C_{20}$ olefins | 0.1 |
| other compounds | 0.1 |

*) quantitative analyses of cis- and trans-2-olefins are carried out separately

Dimerization of the distilled monomer fraction was carried out in a flow reactor (120° C.) as described in section a) of the present example. Total $C_{16}$ conversion and selectivities for different reaction products are shown in the table 5 below.

TABLE 5

Dimerization of recycled $C_{16}$ hydrocarbons

| | Time (TOS)/h | | |
|---|---|---|---|
| | 6 | 24 | 48 |
| Total $C_{16}$ conversion/(%) | 36.3 | 25.6 | 12.2 |
| Selectivity/(%) | | | |
| light products (<C16) | 0.0 | 0.0 | 0.0 |
| $C_{16}$-$C_{32}$ | 0.0 | 0.0 | 0.0 |
| dimers | 86.1 | 88.5 | 90.6 |
| trimers | 11.5 | 10.2 | 8.9 |
| heavier (>C48) | 2.4 | 1.3 | 0.6 |

Example 3

Hydrogenation of the Dimerized Products, and Properties of the Produced Base Oil Product The dimerized product of example 2, separated by distillation, and the bottom product of the distillation were hydrogenated as separate batches in a batch reactor using a heterogeneous nickel catalyst. In the hydrogenation, the reaction time was 2 hours, the temperature was 200° C., and the pressure was 50 bar. The properties of the hydrogenated dimer and the bottom product are presented in table 6 below.

TABLE 6

Hydrogenated dimer and hydrogenated bottom product

| Property/unit | Method | Hydrogenated dimer product | Hydrogenated bottom product |
|---|---|---|---|
| Lighter than the dimer/ % by weight | ASTM D2887 | 0.2 | 0.0 |
| Dimer/% by weight | ASTM D2887 | 99.6 | 49.9 |
| Trimer/% by weight | ASTM D2887 | 0.2 | 39.7 |
| Tetramer and heavier/ % by weight | ASTM D2887 | 0.0 | 10.4 |
| Viscosity at 100° C./ cSt | ASTM D 445 | 4.241 | 6.916 |
| Viscosity at 40° C./cSt | ASTM D 445 | 18.27 | 36.85 |
| Viscocity index (VI) | ASTM D 2270 | 142 | 150 |
| Noac evaporation loss/ % by weight | CECL-40-93-B | 7.9 | not determined |
| Pour point/° C. | ASTM D2887 | −24 | −12 |

Example 4

Regeneration of the Catalyst

In the dimerization according to example 2 a), the hydrocarbon stream was stopped after 96 hours. Thereafter, the catalyst was purged with nitrogen stream (30 l/h) for 1.5 hours at 200° C. At the beginning of the regeneration, the nitrogen stream was replaced with a stream of synthetic air (8 l/h). The reactor was heated from 200° C. to 500° C. with the temperature elevation rate of 1.5° C./min. The regeneration was continued for 2 hours at 500° C. Then, the temperature was reduced again to 200° C., and the air stream was replaced with nitrogen stream (30 l/h) for 1 hour. Dimerization was carried out using the regenerated catalyst in a flow reactor (120° C.) as described in example 2 a). The results are shown in table 7 below.

TABLE 7

Dimerization of 1-hexadecene

| | Time (TOS)/h | |
|---|---|---|
| | 6 | 24 |
| Total $C_{16}$ conversion/(%) | 47.0 | 40.4 |
| Selectivity/(%) | | |
| light products (<C16) | 0.0 | 0.0 |
| $C_{16}$-$C_{32}$ | 0.0 | 0.0 |
| dimers | 81.5 | 83.3 |
| trimers | 3.5 | 13.4 |
| heavier (>C48) | 3.5 | 3.4 |

Example 5

Dimerization in a Flow Reactor Using a Mesoporous Catalyst

A flow reactor was packed with a fresh mesoporous H-MM-4MW22-2A1 catalyst (mesoporous molecular sieve embedded with zeolite, the production of which is described in the patent application FI 20041675) (5 g) having an aluminium content of 2.2% by weight, number of acid sites of 180 µmol/g, and mesoporous surface area of >700 m², diluted with silicon carbide (support) (V (catalyst):V (SiC)=1:3). Dimerization of 1-hexadecene was performed using the mesoporous H-MM-4MW22-2A1 catalyst in the flow reactor (120° C.) as described in the example 2 a). The results are shown in the table 8 below.

TABLE 8

Dimerization of 1-hexadecene

| | Time (TOS)/h | | |
|---|---|---|---|
| | 6 | 24 | 48 |
| Total $C_{16}$ conversion/(%) | 57.6 | 44.1 | 31.8 |
| Selectivity/(%) | | | |
| light products (<C16) | 0.0 | 0.0 | 0.0 |
| $C_{16}$-$C_{32}$ | 0.0 | 0.0 | 0.0 |
| dimers | 89.3 | 91.6 | 93.3 |
| trimers | 10.0 | 7.7 | 6.0 |
| heavier (>C48) | 0.6 | 0.7 | 0.7 |

Example 6

Regeneration of the H-MM-4MW22-2A1 Catalyst

The H-MM-4MW22-2A1 catalyst used in example 5 was regenerated using the regenerating treatment described in example 4. Dimerization of 1-hexadecene was performed using this mesoporous H-MM-4MW22-2A1 catalyst in the flow reactor (120° C.) as described in the example 2 a). The results are shown in table 9.

TABLE 9

Dimerization of 1-hexadecene in a flow reactor

| | Time (TOS)/h | | |
|---|---|---|---|
| | 6 | 24 | 48 |
| Total $C_{16}$ conversion/(%) | 53.5 | 36.9 | 31.5 |
| Selectivity/(%) | | | |
| light products (<C16) | 0.0 | 0.0 | 0.0 |
| $C_{16}$-$C_{32}$ | 0.0 | 0.0 | 0.0 |
| dimers | 89.2 | 92.0 | 92.5 |
| trimers | 9.9 | 7.5 | 6.5 |
| heavier (>C48) | 0.9 | 0.5 | 0.9 |

Example 7

Hydrogenation of the Dimerization Products, and Properties of the Base Oil Product Products from examples 6 and 7 were pooled (1448 g). From the pooled product, unreacted $C_{16}$ fraction (980 g) was separated by distillation, and from the bottom product containing dimers (462 g) middle fraction (6 g) was separated. The bottom product containing dimers was hydrogenated according to example 3. Table 10 shows the composition and properties of the hydrogenated bottom product.

TABLE 10

Hydrogenated bottom product

| Property/unit | Method | Hydrogenated bottom product containing dimers |
|---|---|---|
| Lighter than the dimer/wt. % | ASTM D2887 | 0.0 |
| Dimer/wt. % | ASTM D2887 | 90.8 |
| Trimer/wt. % | ASTM D2887 | 8.3 |
| Tetramer and heavier/wt. % | ASTM D2887 | 0.9 |
| Viscosity at 100° C./cSt | ASTM D 445 | 4.577 |
| Viscosity at 40° C./cSt | ASTM D 445 | 20.41 |
| Viscocity index (VI) | ASTM D 2270 | 144 |
| Noac evaporation loss/wt. % | CECL-40-93-B | 7.4 |
| Pour point/° C. | ASTM D2887 | −21 |

Example 8

Dimerization of 1-Decene in a Catalytic Distillation Reactor

Dimerization of 1-decene was carried out in a catalytic distillation reactor where the catalyst was placed inside a distillation column, the amount of the catalyst being 4% by weight based on the amount of 1-decene. An aluminium silicate catalyst (Nikki Chemical Co. Ltd.) was used as the catalyst. FIG. 4 graphically shows the comparison of the reactions either carried out in a batch reactor at a temperature of 120° C., or in a catalytic distillation reactor at the same temperature, respectively using the same catalyst/feedstock level. As can be seen from FIG. 4, with the same conversion, a dimer selectivity of more than 90% may be attained using a catalytic distillation apparatus, while selectivities in the batch experiment were below 80% at identical temperatures.

Example 9

Effect of Pressure on the Dimer Yield in a Catalytic Distillation Apparatus Dimerization of 1-decene was carried out in a catalytic distillation apparatus where the catalyst was placed inside a distillation column, the catalyst being amorphous aluminium silicate (Nikki Chemical Co. Ltd.), the amount thereof being 4% by weight based on the amount of 1-decene. The conversion of 1-decene was raised to the desired level by adjusting the pressure of the catalytic distillation apparatus. During the experiment, the pressure was adjusted to values ranging between 0.17 and 1 bar, the temperature at the bottom of the distillation column elevating from 80 to 300° C. Diner selectivity for all conversion levels was >80%. Base oil yield was 92% for the decene conversion of 94%.

Example 10

Dimerization of 1-Hexadecene in a Catalytic Distillation Reactor

Dimerization of 1-hexadecene was performed in a catalytic distillation apparatus where the catalyst was placed in a distillation column, the amount of the catalyst being 6.5% by weight of 1-hexadecene. The catalyst was amorphous aluminium silicate (Nikki Chemical Co. Ltd.). The pressure during the experiment was 0.002 bar, the temperature at the bottom being elevated from 130° C. to 235° C. as the dimerization reaction proceeded. Diner selectivity for all conversion levels was >80%. Base oil and dimer yields were 99% and 82%, respectively, for the hexadecene conversion of 99.3%.

The invention claimed is:

1. A process for producing polyolefins, which process comprises dimerizing a feedstock comprising an n-olefin or a mixture of n-olefins in the presence of a solid acidic catalyst by passing the feedstock to a catalytic distillation apparatus comprising either a) a combination of a distillation column and a reactor comprising at least one catalyst bed, or b) a distillation column connected to one or more side reactors comprising at least one catalyst layer, recovering the unreacted n-olefin at the upper part of the distillation column or at the upper part of the combination of the distillation column and the reactor as a side stream to be combined with the feedstock wherein from 50 to 95% by weight of n-olefin monomers from said feedstock contact the catalyst layer more than once, and hydrogenating the reaction product from the dimerization, wherein the catalyst layer comprises solid acidic catalyst material with a mesoporous surface area of more than 100 m$^2$/g, an aluminium content between 0.2 and 30% by weight, the amount of the acid sites of the material ranging between 50 and 500 µmol/g, and the material being selected from the group consisting of acidic amorphous aluminium silicates and mesoporous molecular sieves imbedded with zeolite.

2. The process according to claim 1, wherein the feedstock comprises at least one n-olefin selected from the group consisting of $C_8$-$C_{30}$ n-olefins.

3. The process according to claim 1, wherein in said mesoporous molecular sieves imbedded with zeolite, the mesoporous molecular sieve is MCM-41 with a regular molecular structure.

4. The process according to claim 1, wherein the mesoporous surface area of the catalyst material is more than 300 m$^2$/g.

5. The process according to claim 1, wherein the catalyst material is amorphous aluminium silicate with a mesoporous surface area of more than 300 m$^2$/g.

6. The process according to claim 1, wherein part of the side stream is removed from the distillation column or the combination of the distillation column and the reactor at the upper part thereof.

7. The process according to claim 1, wherein a solvent or a solvent mixture selected from the group of hydrocarbons is added to the feedstock.

8. The process according to claim 1, wherein the feedstock is subjected to drying.

9. The process according to claim 1, wherein the dimerization is performed at a temperature ranging between 25 and 200° C., and at a pressure ranging between 0.001 mbar and 50 bar.

10. The process according to claim 9, wherein said temperature ranges between 50 and 150° C. and said pressure ranges between 0.5 bar and 30 bar.

11. The process according to claim 1, wherein the hydrogenation is performed at a pressure ranging between 5 and 100 bar, and at a temperature ranging between 100 and 400° C., in the presence of a hydrogenation catalyst.

12. The process according to claim 11, wherein said pressure is between 10 and 70 bar and said temperature is between 150 and 250° C.

13. The process according to claim 1, wherein the feedstock comprises 1-decene.

14. The process according to claim 1, wherein the feedstock comprises 1-hexadecene.

15. The process according to claim 1, wherein the feedstock comprises olefins of natural origin produced from biological starting materials.

16. The process according to claim 1, wherein distillation is carried out after the dimerization or the hydrogenation or after both.

17. The process according to claim 1, wherein base oil or base oil component is produced with said process.

\* \* \* \* \*